United States Patent
MacKenzie et al.

(10) Patent No.: US 6,833,540 B2
(45) Date of Patent: *Dec. 21, 2004

(54) SYSTEM FOR MEASURING A BIOLOGICAL PARAMETER BY MEANS OF PHOTOACOUSTIC INTERACTION

(75) Inventors: Hugh Alexander MacKenzie, North Berwick (GB); John Matthew Lindberg, Grayslake, IL (US)

(73) Assignee: Abbott Laboratories, Abbott Park, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 10/165,941

(22) Filed: Jun. 10, 2002

(65) Prior Publication Data

US 2003/0010898 A1 Jan. 16, 2003

Related U.S. Application Data

(62) Division of application No. 09/380,640, filed on Apr. 25, 2000, now Pat. No. 6,403,944.

(30) Foreign Application Priority Data

Mar. 7, 1997 (GB) .............................................. 9704737

(51) Int. Cl.⁷ ............................................. H01L 31/00
(52) U.S. Cl. .................................... 250/214.1; 250/239
(58) Field of Search ............................. 250/239, 214.1, 250/556, 461.2, 338.5, 227.14, 227.19, 227.24; 356/39–41; 128/665–667, 903

(56) References Cited

U.S. PATENT DOCUMENTS

| | | |
|---|---|---|
| 5,074,309 A | 12/1991 | Gerdt |
| 5,151,590 A | 9/1992 | Takamoto et al. |
| 5,348,002 A | 9/1994 | Caro |
| 5,348,003 A | 9/1994 | Caro |
| 5,579,001 A | 11/1996 | Dempsey et al. |
| 5,702,284 A | 12/1997 | Gallegos |
| 5,786,592 A | 7/1998 | Hok |
| 5,840,023 A * | 11/1998 | Oraevsky et al. ........... 600/407 |
| 6,292,680 B1 * | 9/2001 | Somogyi et al. ............ 600/407 |

FOREIGN PATENT DOCUMENTS

| | | |
|---|---|---|
| DE | 44 00 674 | 7/1995 |
| EP | 0 282 234 | 9/1988 |
| EP | 0 413 330 | 2/1991 |
| EP | 829 224 | 3/1998 |
| FR | 2728452 | 7/1997 |
| JP | 01/191/040 | 8/1989 |
| JP | 06 317 566 | 11/1994 |
| JP | 07 136 150 | 5/1995 |

OTHER PUBLICATIONS

Christison, "Laser photoacoustic determination of physiological glucose concentrations in human whole blood", *Medical & Biological Engineering & Computing*, 31(3):284–290 (1993)month unknown.

Mandelis, "Frequency modulated (FM) time delay photoacoustic and photothermal wave spectroscopies. Technique, instrumentation, and detection Part 1: Theoretical", *Review of Scientific Instruments*, 57(4): 617–621 (1986) month unknown.

Poulet and Chambron, "In vivo cutaneous spectroscopy by photoacoustic detection", *Medical & Biological Engineering & Computing*, 23:585–588 (1985) month unknown.

Spanner, et al., "Noninvasive determination of blood constituents using an array of modulated laser diodes and a photoacoustic sensor head", *Fresenius J. Anal. Chem.*, 355:327–328 (1996)month unknown.

PCT International Search Report Jul. 3, 1997.

* cited by examiner

*Primary Examiner*—Que T. Le
(74) *Attorney, Agent, or Firm*—David L. Weinstein

(57) ABSTRACT

A system for measuring a biological parameter, such as blood glucose, the system comprising the steps of directing laser pulses from a light guide into a body part consisting of soft tissue, such as the tip of a finger to produce a photoacoustic interaction. The resulting acoustic signal is detected by a transducer and analyzed to provide the desired parameter.

21 Claims, 16 Drawing Sheets

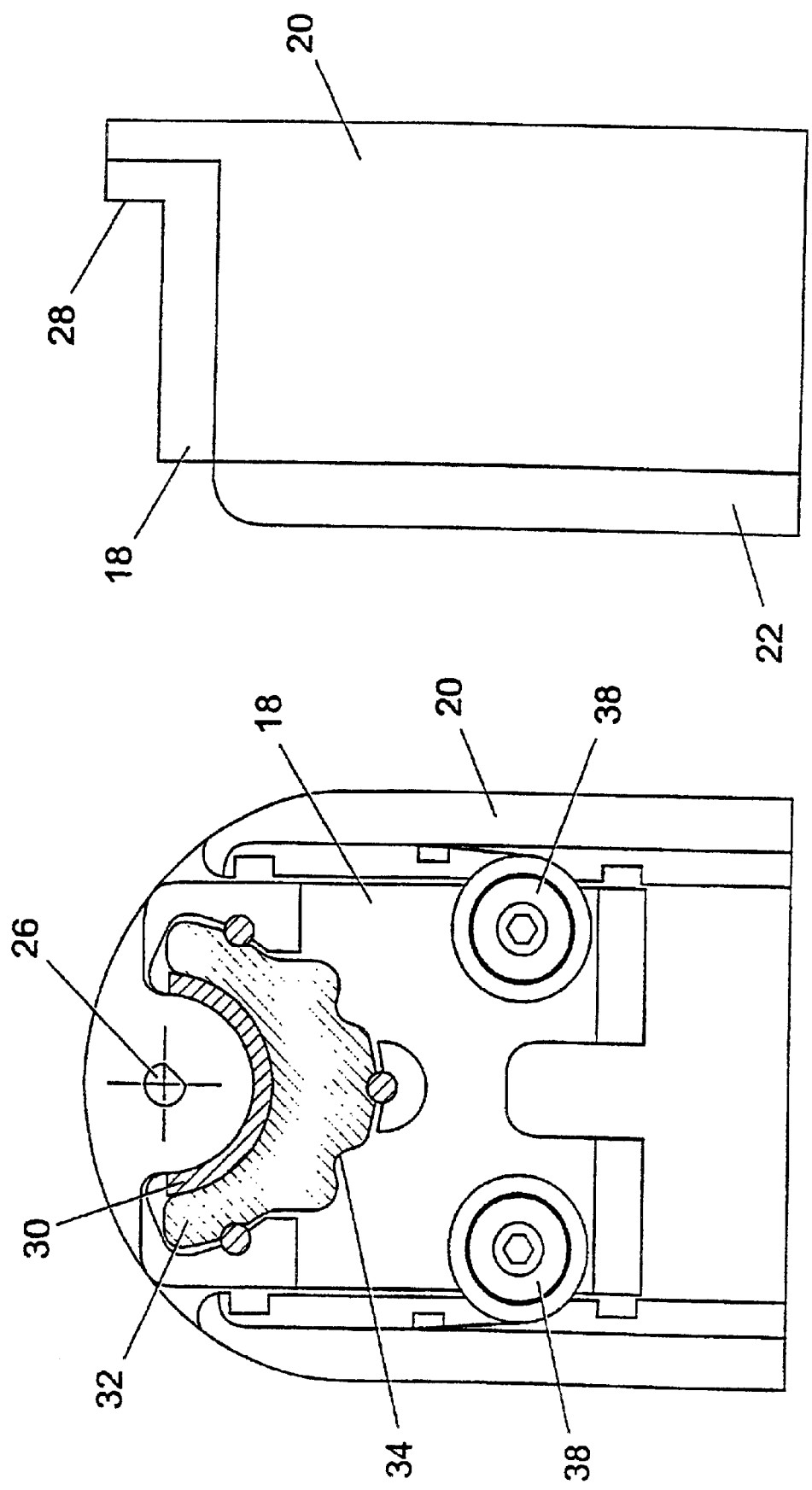

US 6,833,540 B2

SYSTEM FOR MEASURING A BIOLOGICAL PARAMETER BY MEANS OF PHOTOACOUSTIC INTERACTION

This application is a divisional of U.S. Ser. No. 09/380,640 filed Apr. 25, 2000 now U.S. Pat. No. 6,403,944.

BACKGROUND OF THE INVENTION

1. Field of the Invention

This invention relates to apparatus for use in non-invasive in vivo monitoring of physiological substances such as blood and the like.

2. Discussion of the Art

One particular, but not exclusive, application of the present invention is in the monitoring of blood glucose, for example in the management of diabetes mellitus. It is accepted that the management of diabetes can be much improved by routine monitoring of blood glucose concentration and clinicians suggest that monitoring as often as four times per day is desirable.

The monitoring technique currently available for use by patients involves using a spring loaded lancet to stab the finger to obtain a blood sample which is transferred to a glucose test strip. The concentration is derived either by reading the test strip with a reflectance meter or by visual comparison of colour change against a colour scale. Many diabetics find the testing onerous as the technique is painful, inconvenient, messy, potentially embarrassing and offers a site for the transmittance and acceptance of infection.

Techniques have also been developed for non invasive measurement using transmittance or reflectance spectroscopy. However the required instruments are expensive and it is difficult to obtain accurate and repeatable measurements.

There are also known various types of in vivo chemical sensors. These rely on implanting minimally invasive sensors under the skin surface, but such sensors have poor long term reproducibility and bio-compatibility problems.

There is therefore a need for improved means for routine monitoring of blood glucose in a manner which is simple and straightforward to use.

The present invention makes use of photoacoustic techniques. The fundamentals of photoacoustic techniques are well known per se. A pulse of light, typically laser light, is applied to a substance containing an analyte of interest in solution or dispersion, the wavelength of the applied light being chosen to interact with the analyte. Absorption of the light energy by the analyte gives rise to microscopic localised heating which generates an acoustic wave which can be detected by an acoustic sensor. These techniques have been used to measure physiological parameters in vitro.

U.S. Pat. Nos. 5,348,002 and 5,348,003 (Caro) propose the use of photoacoustics in combination with photoabsorption for the measurement of blood components in vivo. However, the arrangement proposed by Caro has not been demonstrated as a workable system and may suffer from interference to a degree which would preclude useful acoustic signals, and since they would also suffer from interference and resonance effects from hard structures such as bone.

It has also been proposed by Poulet and Chambron in *Medical and Biological Engineering and Computing*, November 1985, Page 585 to use a photoacoustic spectrometer in a cell arrangement to measure characteristics of cutaneous tissue, but the apparatus described would not be suitable for measuring blood analytes.

Published European Patent Application 0282234A1 (Dowling) proposes the use of photoacoustic spectroscopy for the measurement of blood analytes such as blood glucose. This disclosure however does not show or suggest any means which would permit the required degree of coupling to body tissues for use in vivo.

SUMMARY OF THE INVENTION

Accordingly, the present invention provides a sensor head for use in photoacoustic in vivo measurement, comprising a housing shaped to engage a selected body part, light transmission means terminating in said housing so as to transmit light energy form a light source to enter the body part along a beam axis, and acoustic transducer means mounted in the housing to receive acoustic waves generated by photoacoustic interaction within the body part, the acoustic transducer means being disposed in the housing to receive said acoustic wave in a direction of high acoustic energy.

The expression "direction of high acoustic energy" is used herein to denote a direction other than the forward direction of the light beam. Preferably, the transducer means is disposed so as to intercept acoustic energy propagating at right angles to the optical beam axis, or at an angle to the optical beam axis which may be down to about 20°, typically about 45°.

An exact measure of the angle of high acoustic energy can be worked out but is dependent upon the specific geometry of the light source, the properties of the tissue and the absorption coefficient of the tissue. One model for understanding the propagation of the acoustic energy in any homogenous media was developed by Huyghens and is called the principle of superposition. In this model each volume element that is illuminated by the light generates an acoustic pressure wave that radiates outward in a spherical manor. The magnitude of the pressure wave at each volume element depends on the intensity of the optical beam at that location, the absorption coefficient of the material at that location, the wavelength of light and on several other physical properties of the material such as the speed of sound and the specific heat. The signal measured at the detector is just the superposition of all pressure waves from all points that are illuminated by the source light. An analytical solution for the pressure wave has been worked out for a few cases in aqueous material. The analytical case that best matches the in-vivo measurements is that of a cylindrical optical beam propagating in a weekly absorbing material. In this case the direction of highest acoustic energy is perpendicular to the optical axis. The base detector location is with the plane of the detector perpendicular to the acoustic energy, or parallel to the optical axis. This is because the acoustic detector has the highest sensitivity when the acoustic energy strikes the detector perpendicular to the plane of the detector. This analytical model is not completely accurate for the in-vivo measurement case because of scattering of the tissue and because the tissue absorbs more than the model predicts. These differences indicate that a different position for the detector will be optimal. A detailed numeric model is required to determine the best detector location and is dependent upon the beam properties (focused to a point, colligated, etc.), body site (finger, earlobe, arm etc.) and wavelength. One skilled in the art can readily develop an appropriate mode. However, suitable locations for a detector will generally be at an angle to the optical axis. Angles between 40 and 90 degrees should be suitable.

In one preferred arrangement, the acoustic transducer means is arranged parallel to the optical beam axis. This arrangement is particularly suitable for use where the selected body part is the distal portion of a finger, in which case the housing may include a generally half-cylindrical depression in which the finger may be placed with the light transmission means aimed at the end of the finger.

Preferably, the acoustic transducer means comprises a piezoelectric transducer which most preferably is of a semi-cylindrical shape. This transducer may be provided with a backing of lead or other dense material, and the backing may have a rear surface shaped to minimise internal acoustic reflection.

Alternative transducer means include a capacitor-type detector, which is preferably small and disk-shaped; an integrated semiconductor pressure sensor; and an optical pressure sensor, for example based on an optical fibre.

In an alternative arrangement, the plane of the transducer may be arranged to be perpendicular to the optical axis to detect the acoustic wave which is propagating in a direction opposite to the direction of the light beam. For example, the acoustic transducer means may be part-spherical with an aperture to allow access for the light beam. This may be particularly suitable for engagement with a body part other than the finger, for example the back of the arm.

The generation of a surface acoustic wave is an inherent aspect of the in vivo pulsed photoacoustic generation in tissue and may be used to characterize tissue properties such as density. A surface wave detector may be provided in the sensing head assembly.

Preferably means are provided for ensuring a consistent contact pressure between the selected body part and the acoustic transducer means. In the case where the selected part is the distal portion of the finger, said means may be provided by mounting the portion of the housing engaged by the finger in a resiliently biased fashion against the remainder of the housing, and providing means to ensure that measurement is effected when the predetermined force or pressure is applied by the subject against the resilient bias. In the case where the selected part is the earlobe, said means may be provided by placing the ear between two plates and applying pressure to the ear with springs or weights or other force method. The two plates holding the ear may contain a removable insert. The two plates may be flat or may be of another shape to optimally position the detector with respect to the beam axis.

In addition, the present invention provides a sensor head for use in photoacoustic in-vivo measurements, comprising a housing shaped to receive a removable insert, a removable insert that engages a selected body part, the insert being fitted to an individual, allowing for a range of sizes of body parts to be used, and further comprising light transmission means terminating in or near said removable insert so as to transmit light energy from a light source or sources to enter the body part along a beam axis, and an acoustic transducer means mounted in the housing or in the removable insert to receive acoustic waves generated by photoacoustic interaction within the body part to receive said acoustic waves in a direction of high acoustic energy.

From another aspect the present invention provides an in vivo measuring system comprising a sensor head as hereinbefore defined in combination with a light source coupled with the light transmission means, and signal processing means connected to receive the output of the acoustic transducer means and to derive therefrom a measurement of a selected physiological parameter.

Preferably, the light transmission means is a fiber distribution system where each light source is connected to an individual fiber and when multiple light sources are used the multiple fibres are joined by some standard fiber combining method, such as a wavelength division multiplexer or a fiber coupler. The fiber that comes from the light source, or contains the combined light for a multiple source system, is then terminated in proximity to the body part being measured. The fiber could be in contact with the body part or alternatively standard optics, such as lenses, beamsplitters and such, could be employed to convey the light from the end of the fiber to the body part. A reference detector or several reference detectors and beamsplitters can be added to the optical distribution system to determine the energy of the light entering the body part.

Alternatively, the optical distribution system may contain mechanical holders, lenses and such to convey the light from the source, or sources, to a location in proximity to the body part being measured. A reference detector or several reference detectors and beamsplitters can be added to the optical distribution system to determine the energy of the light entering the body part.

The acoustic signal from the detector contains information in both time and frequency, and there may be information from several sources. The processing means is preferably a multi-dimensional processing method, such as Classical Least Squares (CLS) or Partial Least Squares (PLS). Alternatively the processing method may be more flexible, such as a Neural Network. In addition to these methods the signals may be analysed for their frequency content using such techniques as Fourier Analysis or Frequency Filtering In addition techniques may be employed that use time information such as the time delay from source trigger. Techniques that combine both frequency and time information may be employed, such as Wavelet analysis.

The light source is preferably a laser light source and is most suitably a pulsed diode laser, but may utilise a set of such lasers or utilise a tunable laser source. In a particularly preferred form, suitable for use in measuring blood glucose concentration, a laser diode is used with a wave length in the range of approximately 600 nm to 10,000 nm and a pulse duration of the order of 5 to 500 ns.

The delivery to the measurement site may be either directly or by optical fibre with a suitable optical element to focus the beam into the tissue.

Preferably means are provided for time multiplexing multiple sources when multiple sources are used. Each source is switched on, and it generates an optical pulse, or a set of optical pulses. This pulse, or set of pulses, generates an acoustic signal that is detected by the detector. Each source is pulsed in sequence until all sources have been used to generate their own signal.

The measuring system may conveniently be in the form of a self contained system including a power supply and a readout, which may be carried on the person and used at any convenient time.

It is also possible for such a self contained system to incorporate, or to be provided with facilities for connection to, a cellular telephone, two-way pager or other communication device for routine transmission of measurements taken to a central data collection point.

In addition the measuring system may have provision for manipulating the body part under measurement and for performing additional measurement of the tissue to get other information about the state of the physiology of the tissue. It is well-known in the art that squeezing a section of tissue to increase the pressure and then releasing the pressure will cause changes in the total blood volume in the measurement site. The present invention may allow for this type of manipulation including the squeezing of a body part, such as an earlobe, and making photo acoustic measurements at several different pressures. The present invention may also allow for the measurement of the temperature of the body site and to apply a correction to the measurements based upon the temperature of the body site.

Another type of physiological manipulation is body temperature. It is known in the art that several parameters involved in the detection of the photo acoustic signal, such as the speed of sound, are dependent upon the temperature of the medium the signal is propagating through (the tissue). Also the profusion of the blood in the small capillaries is dependent upon the temperature of the tissue. Additional information about the tissue can be obtained if the photo acoustic measurement is made at several temperatures, both higher and lower than ambient temperature. This additional information is used to better eliminate interferences to the determination of the analyte under investigation. These are only two examples of manipulating the body site and are not intended to be an exhaustive list, and they can be used in combination with other manipulation techniques.

The in-vivo measuring system may comprise a means for storing calibration coefficients or operation parameters or both calibration coefficients and operational parameters, in order to calibrate the instrument and to set critical operational parameters.

Another aspect of the present invention provides a means for adjusting the calibration coefficients and operational parameters to be specific to a particular person and may be used to adjust for such things as body part size, skin color, skin condition, amount of body fat, efficiency of the detector and efficiency of the source(s).

In addition the present invention may provide for having the specific calibration coefficients and operational parameters be contained in a storage site located in the removable insert. This allows for the system to be both mechanically and operationally configured to a particular individual. Additionally the invention may allow for the calibration coefficients and operational parameters to be stored in two locations, one in the non-removable housing and one in the removable insert with some of the coefficients and parameters stored in each location. This allows for reader system coefficients to be stored in the reader and coefficients specific to an individual to be stored in the removable insert for that person, enabling many people to use the same reader.

Another aspect of the present invention provides means for connecting the non-invasive measuring system to an invasive measuring system for the purpose of calibrating or adjusting the operational parameters of the non-invasive measuring system. Such connection may be accomplished, but is not limited to, communication by a wire, IR link or radio waves.

Another aspect of the present invention provides a method for removing instrument drift from the measurement comprising the steps of:
1. Placing a standard in the reader in place of the body part.
2. Measuring the signal from the standard for each wavelength and storing the values in the calibration storage location.
3. Before making a measurement of a body part, placing the calibration standard in the reader.
4. Measuring the signal from the standard for each source.
5. Comparing the just measured standard values to the stored calibration values.
6. Calculating correction factors for each source wavelength.
7. Removing the standard and placing the body part in the reader.
8. Measuring the signal from the body part for each source.
9. Adjusting the measured values using the calculated correction factors.

In addition to the signal correction factors a correction factor can be calculated for the instrument temperature. This can be applied to each signal with a different correction coefficient.

The invention further provides a method of measuring a biological parameter in a subject, the method comprising the steps of:
directing one or more pulses of optical energy from the exterior into the tissue of a subject along a beam axis, the optical energy having a wavelength selected to be absorbed by tissue components of interest, thereby to produce a photoacoustic interaction;
detecting acoustic energy resulting from said photoacoustic reaction by means of a transducer positioned to intercept acoustic energy propagating in a direction other than the forward direction of said beam axis; and
deriving from said detected acoustic energy a measure of the parameter of interest; and a corresponding apparatus.

BRIEF DESCRIPTION OF THE DRAWINGS

Embodiments of the invention will now be described, by way of example only, with reference to the accompanying drawings in which:

FIG. 3. is a cross section view of the sensor head of FIG. 2;

FIG. 4 is a side view of the sensor head of FIG. 2;

DETAILED DESCRIPTION

Figure 1A:
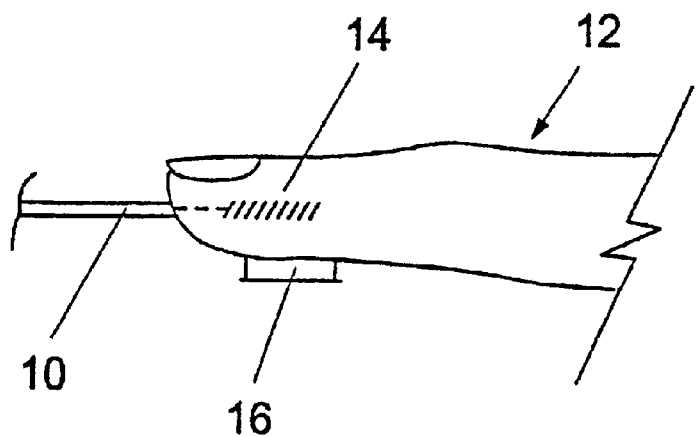
FIGS. 1A, 1B and 1C are side views illustrating the principle of operation of one embodiment of the present invention.

Referring to FIG. 1, an important feature of the present invention lies in introducing light energy along an axis into an area of soft tissue and detecting the resulting acoustic response transverse to that axis. Accordingly, in the arrangement of FIG. 1A light energy from a diode laser (not shown) is transmitted via a fibre-optic guide 10 to the tip of a finger 12. The photoacoustic interaction occurs in an approximately cylindrical region indicated at 14 from which acoustic energy is radiated in a generally cylindrical manner and is detected by a transversely arranged acoustic transducer 16.

Figure 1B:
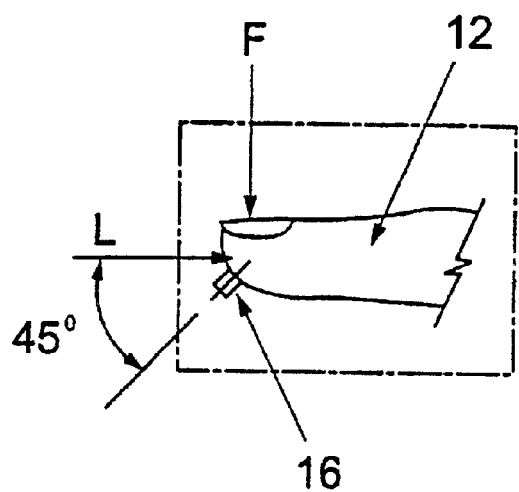
Figure 1C:
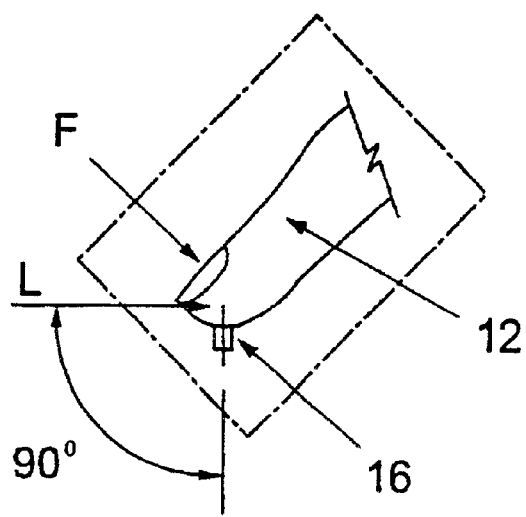

In FIGS. 1B and 1C, the principle is similar. The finger 12 is pressed against a support with force F. In FIG. 1B, the incident light beam indicated at L is directed as in FIG. 1A, and the transducer 16 is at an angle of 45 degrees thereto. In FIG. 1B, the angle is 90 degrees as in FIG. 1A, but the incident beam is directed differently into the fingertip.

In the present embodiment, the laser wavelength is chosen to achieve high degree of absorption by glucose present in the blood. A suitable wavelength is in the range approximately 1000 to 3000 nm. The laser pulse duration is chosen to be short, typically of the order of 5 to 500 ns, in order to minimise thermal diffusion and thus to optimise the acoustic waveform. For the same reasons, it is desirable to use a spot size which is sufficiently small to minimise thermal diffusion, typically a spot size of the order of 0.05 mm to 0.50 mm.

The efficiency of the photoacoustic detection is also influenced by the positioning and dimensions of the acoustic transducer in relation to the characteristic extinction length of the tissue at the principal wavelengths chosen for measurement. In the fingertip arrangement of FIG. 1, the system efficiency will be improved by optimising the length of the transducer crystal parallel to the axis of the finger, but the length should not be so great as to give rise to undesired signals which would occur at the point of entry of the optical energy into the finger and by reason of interaction of the acoustic energy with bone or other hard tissue.

A second limit on the size of the acoustic detector derives from the wavelength of the acoustic wave in the tissue. Again making use of Huyghens principal of superposition we view each point of tissue, that is illuminated by the incoming light, as a point source that generates a spherical pressure wave. The signal measured at the detector is just the superposition of all pressure waves from all points that are illuminated by the source light. Normally if the size of the detector is increased then the signal should also increase because more energy is received by the detector. However if the acoustic detector is too large then a pressure wave generated from a tissue element will create a pressure wave that will strike the both ends of the detector. If the paths length from the tissue element to the first end of the detector is different than the path length to the second end of the detector and if this difference in path length is about one half of the acoustic signal wavelength then the signal will destructively interfere with itself and will reduce the magnitude of the measured signal.

Figure 2:
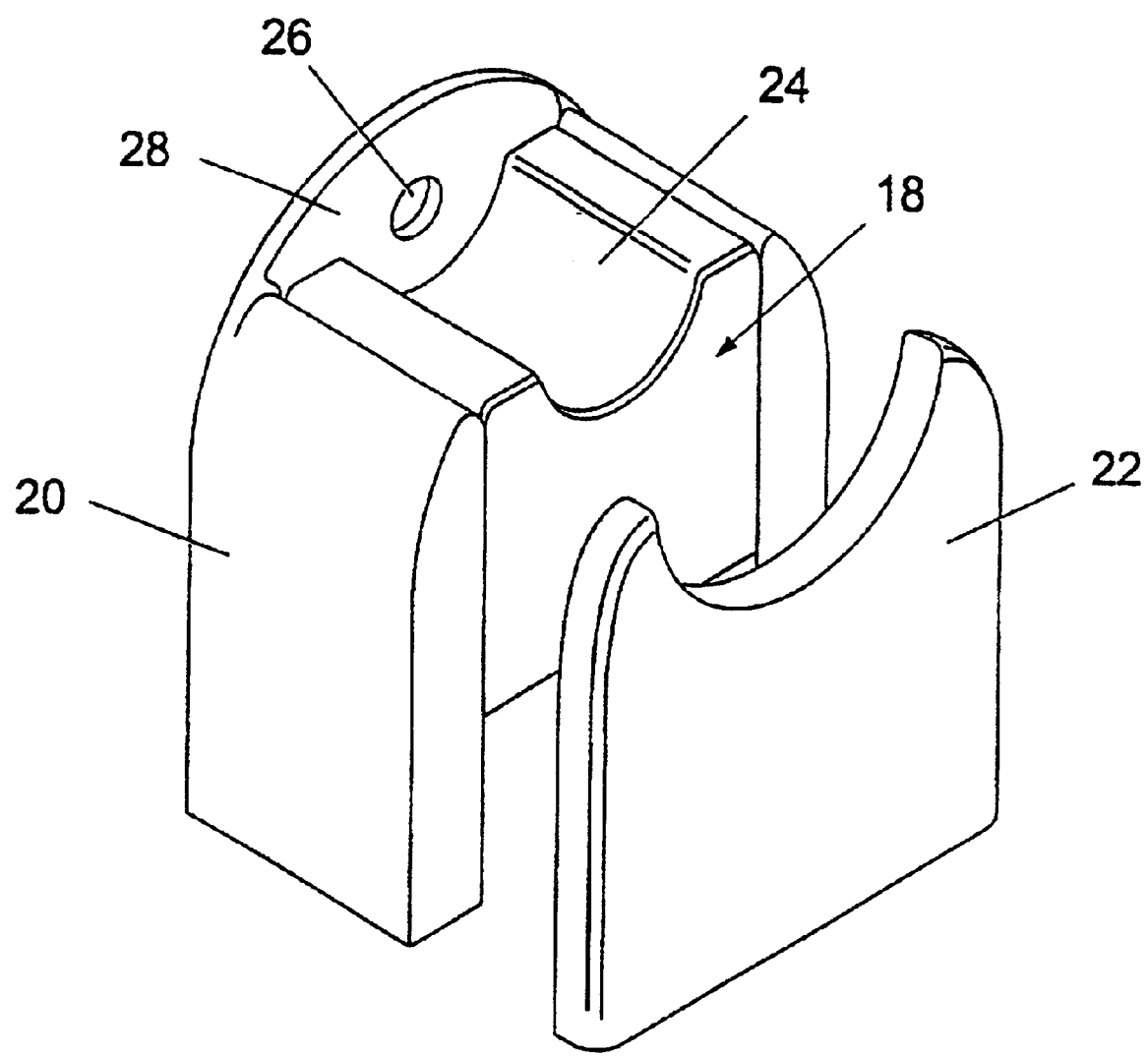
FIG. 2 is a schematic perspective view showing a sensor head for use in carrying out the measurement illustrated in FIG. 1.

Referring to FIG. 2, one manner of carrying out the arrangement shown in FIG. 1 makes use of a sensor head having a finger rest 18 which is slidably moveable within housing 20 closed by a front plate 22. The user inserts his finger in a semi-cylindrical depression 24 in the finger rest 18 with the finger tip engaged against an end surface 28 which includes an exit face 26 of the optical fibre 10. The finger is then pressed downwardly against a resilient bias to enable a standardised contact to be obtained between the skin and the acoustic transducer. The finger tip may first be dipped in water or coated with an aqueous gel to improve the acoustic coupling.

Referring to FIGS. 3 and 4, in this preferred arrangement the acoustic transducer comprises a semi-cylindrical piezo-electric transducer 30. The transducer 30 is provided with a backing member 32 of lead or another dense substance, the rear face 34 of which is shaped in irregular curves. The use of the semi-cylindrical transducer 30 maximises the area for reception of acoustic energy from the finger, while the use of a dense backing material minimises ringing effects within the transducer. Additionally, the rear face 34 is shaped as shown to reduce reflection of acoustic energy back towards the piezo crystal.

FIG. 3 also shows the finger rest biased upwardly by the use of constant tension springs 38.

Figure 5:
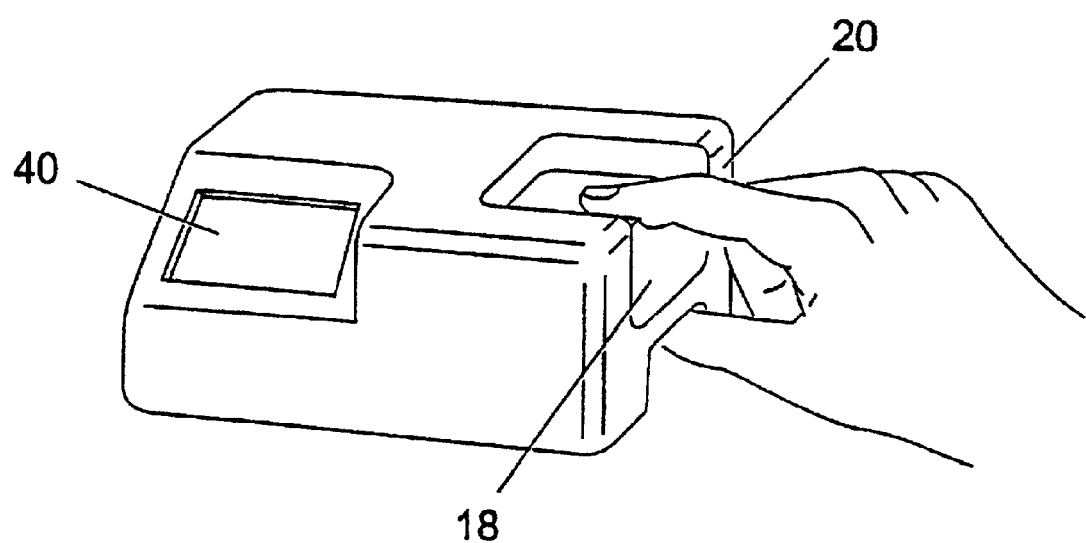
FIG. 5 is a schematic perspective view of an apparatus incorporating the sensor head of FIGS. 2 to 4.

FIG. 5 illustrates schematically the apparatus of FIGS. 2 and 3 embodied in a self-contained, portable blood monitoring apparatus including a user readout 40. An apparatus of this nature allows a diabetic to monitor blood glucose concentration in a convenient manner, as frequently as may be desired, and in a painless and discreet manner.

Figure 6:
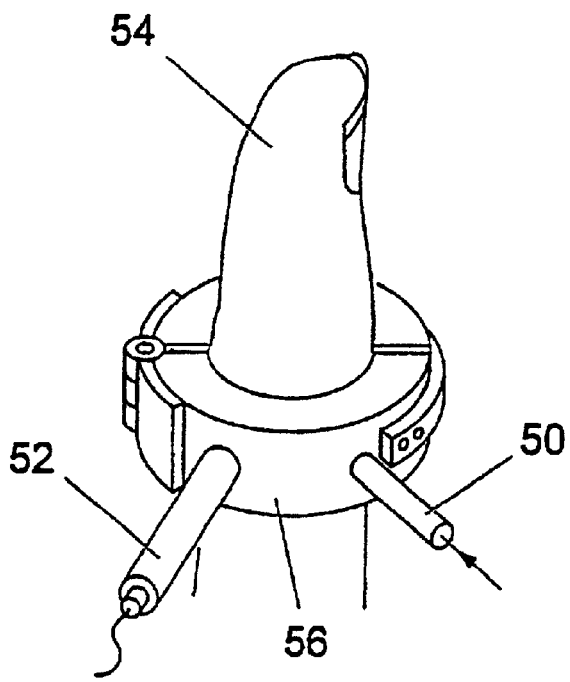
FIG. 6 is a perspective view illustrating an alternative form of sensor head.
Figure 7:
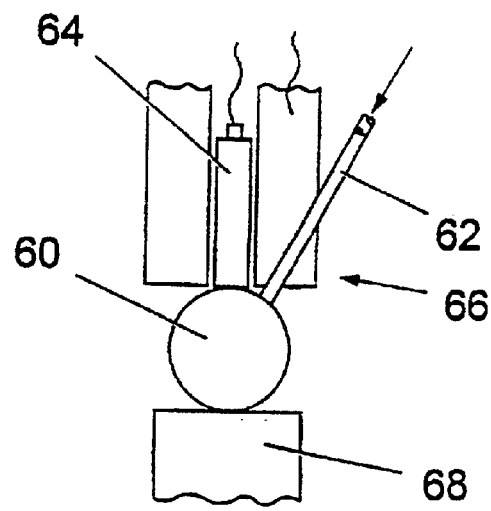
FIG. 7 is a schematic end view showing another form of sensor head.

Other forms of photoacoustic sensor head are possible within the scope of the present invention. For example, FIG. 6 shows an arrangement in which a light guide 50 and an acoustic transducer 52 are applied to a finger 54 by means of a hinged clamp member 56. FIG. 7 shows a finger 60 engaged by a light guide 62 and an acoustic transducer 64 which are carried on a moveable assembly 66 with the finger 60 being trapped between the moveable assembly 66 and a fixed anvil 68.

Figure 8A:
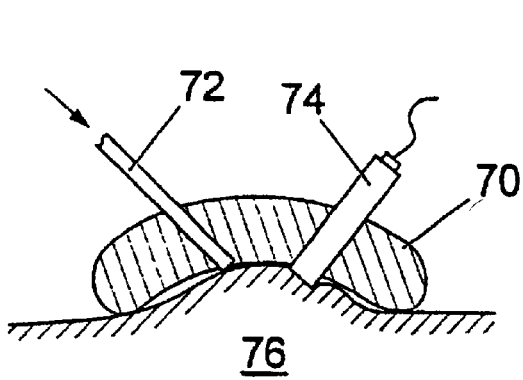
FIGS. 8a and 8b are a cross-sectional side view and a plan view, respectively, of a further sensor head.
Figure 8B:
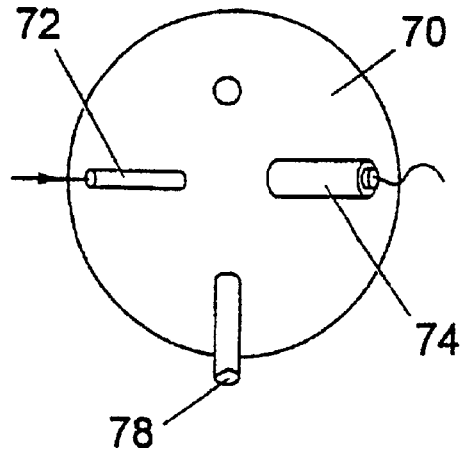

It is also possible to arrange the sensor head to cooperate with a soft tissue surface of the body, for example a soft part of the abdomen. FIGS. 8a and 8b show an arrangement in which a cup shaped member 70, suitably of rubber, causes a light guide 72 and an acoustic transducer 74 to be contacted with a bulge of soft tissue 76 which may for example be drawn into contact by means of a partial vacuum within the member 70 caused by suction through a conduit 78, or by other mechanical or adhesive means.

Figure 9:
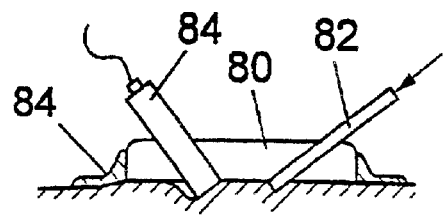
FIG. 9 is a cross-sectional side view of one more embodiment of sensor head.

A somewhat similar arrangement is shown in FIG. 9 in which a planar mount 80 carrying a light guide 82 and acoustic transducer 84 is secured to a soft area of body by means of surgical adhesive 86.

Figure 10:
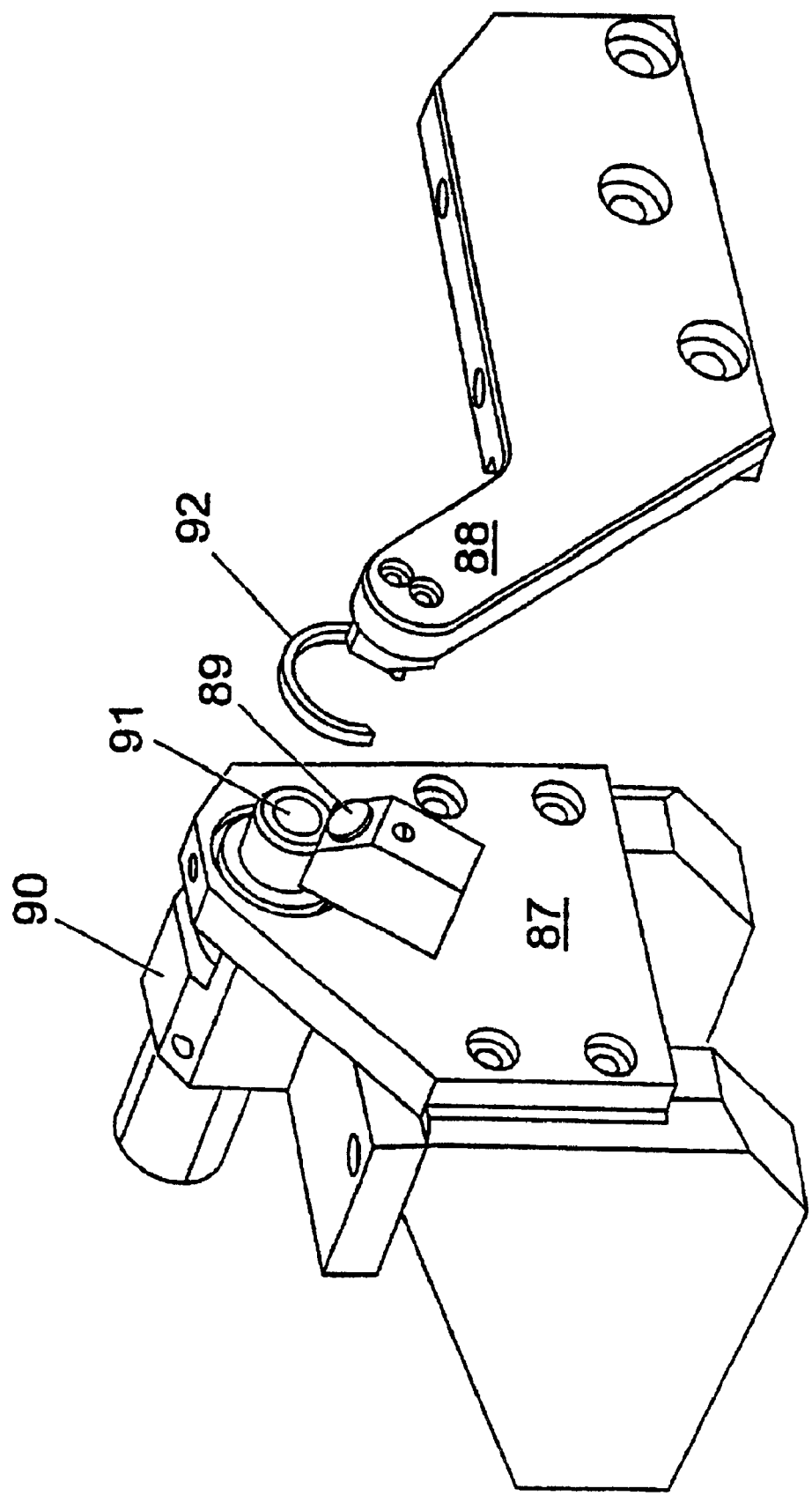
FIG. 10 is a perspective view of one type of ear interface apparatus.

Referring to FIG. 10, one method of performing measurement on an ear lobe involves placing the ear lobe between a fixed plate 87 and a movable plate 88. The acoustic detector 89 is mounted partially perpendicular that is at an acute angle, to the beam axis defined as line going from the center of a lens 90 to the center of a window 91. It has been found that the system works satisfactorily with the detector 89 at an angle or 45° to the beam axis. The window 91 and the detector 89 are placed in direct contact with the ear and the opposite plate 88 places pressure on the ear using a suitable mechanism (not shown). This particular embodiment of the ear interface apparatus incorporates an alignment ring 92 which is temporarily attached to the ear and fits over the window housing 91 to aid in aligning ear into the same location every time.

Figure 11:
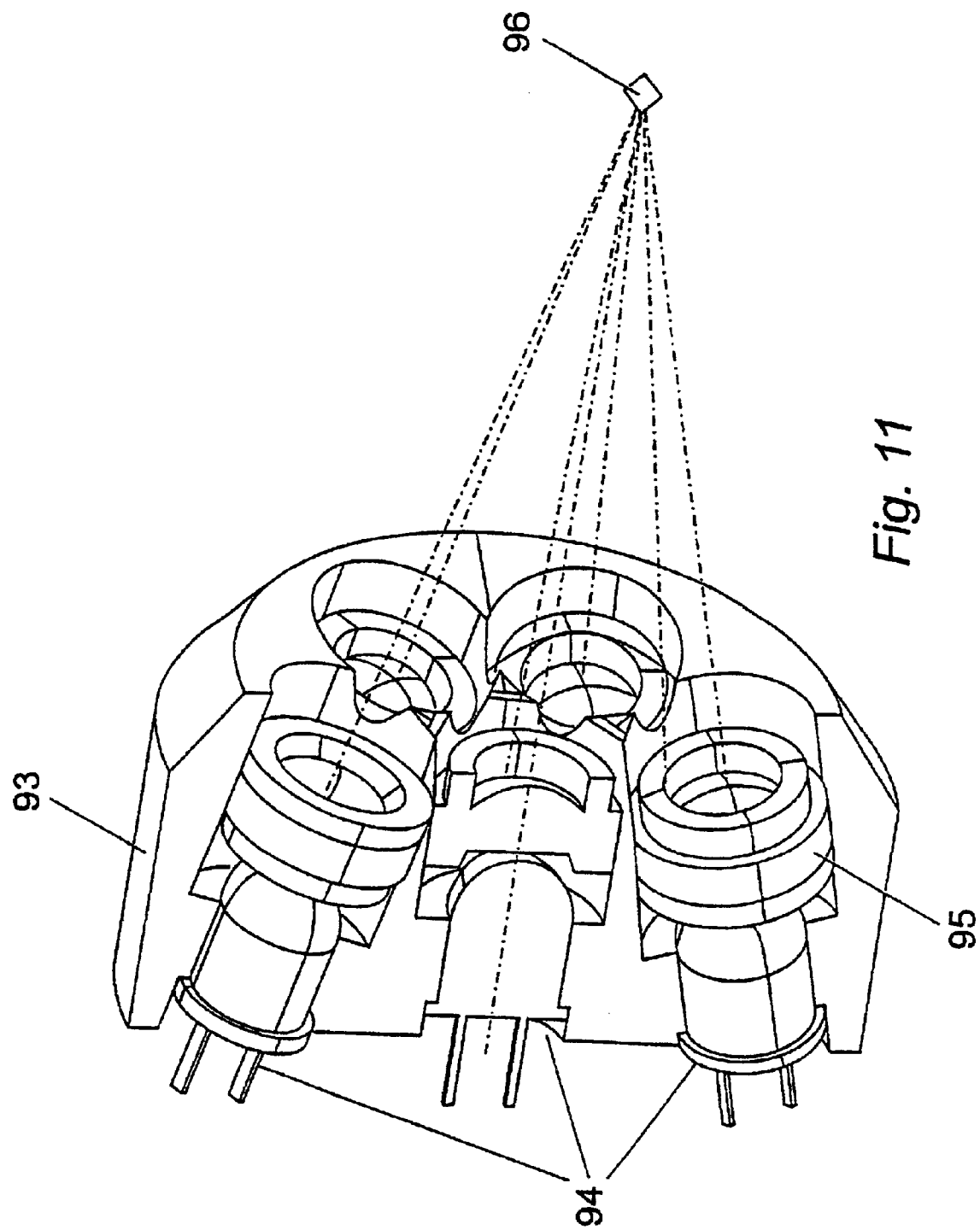
FIG. 11 is a schematic of a multiple laser optical distribution system using lenses, mechanical mounts and a reference detector.

Referring to FIG. 11, one method of combining light sources into the instrument is to use a mechanical housing 93 with several holes used to align lenses 95 and laser diodes 94. The housing shown uses a hexagonal array of seven holes. The sources and lenses are arranged in such a way that they all focus to the same location 96 which could be on the surface of the body part. This design does not show the inclusion of beamsplitters and reference detectors but they can be added in an alternative arrangement.

Figure 12:
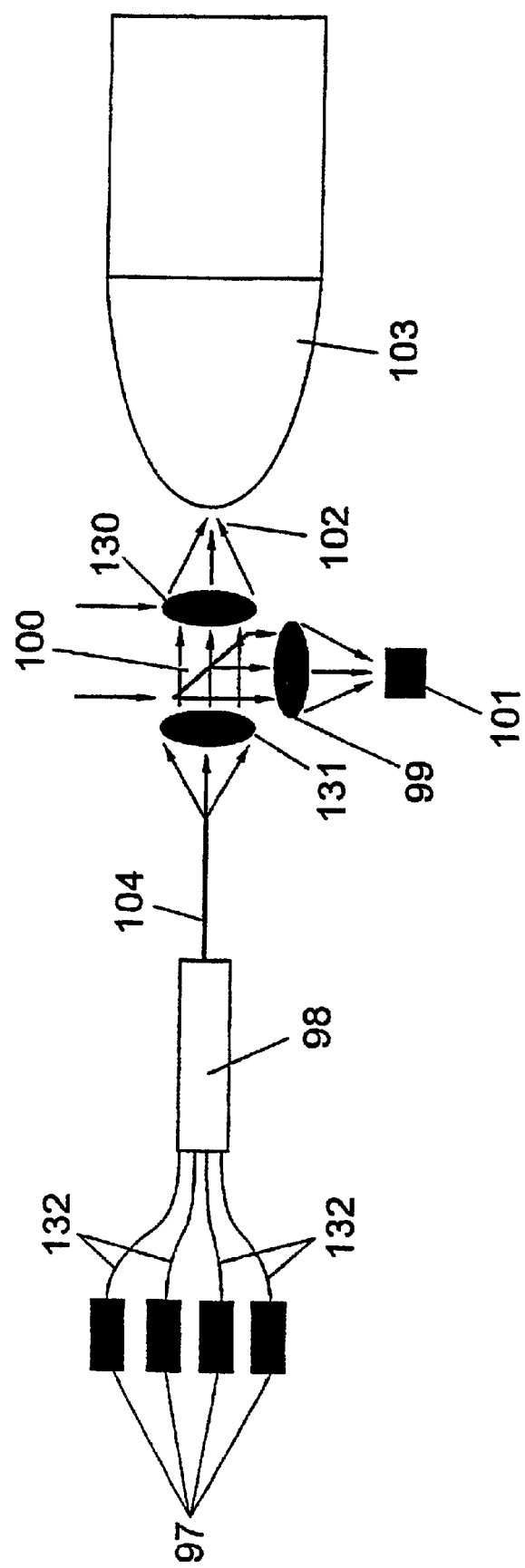
FIG. 12 is a schematic of a multiple laser optical distribution system using fiber optic cables and a fiber Wavelength Division Multiplexer (WDM), a beam splitter and a reference detector.

An alternative method of combining several sources into one beam is shown in FIG. 12. Several laser diodes 97 are shown coupled to individual fiber optic cables 131. These cables 132 are combined using a fiber Wavelength Division Multiplexer (WDM) 98. Alternative combination methods exist including couplers and multi-fiber bundles. The combined light exits the WDM 98 in a single fiber 104 and terminates at the focal point of a lens 131. This end of the fiber is imaged to the end of the finger 103 to a spot 102 using another lens 130. Some of the light is split off the main beam using a beam splitter 100 and focused onto a reference detector 101 using another lens 99. Additional reference detectors and/or beamsplitters can be added to the distribution system without changing its function. Alternatively a reference detector could look directly at the body part to measure the light reflecting off the surface, as a measure of the overall light energy entering the body part.

Figure 13:
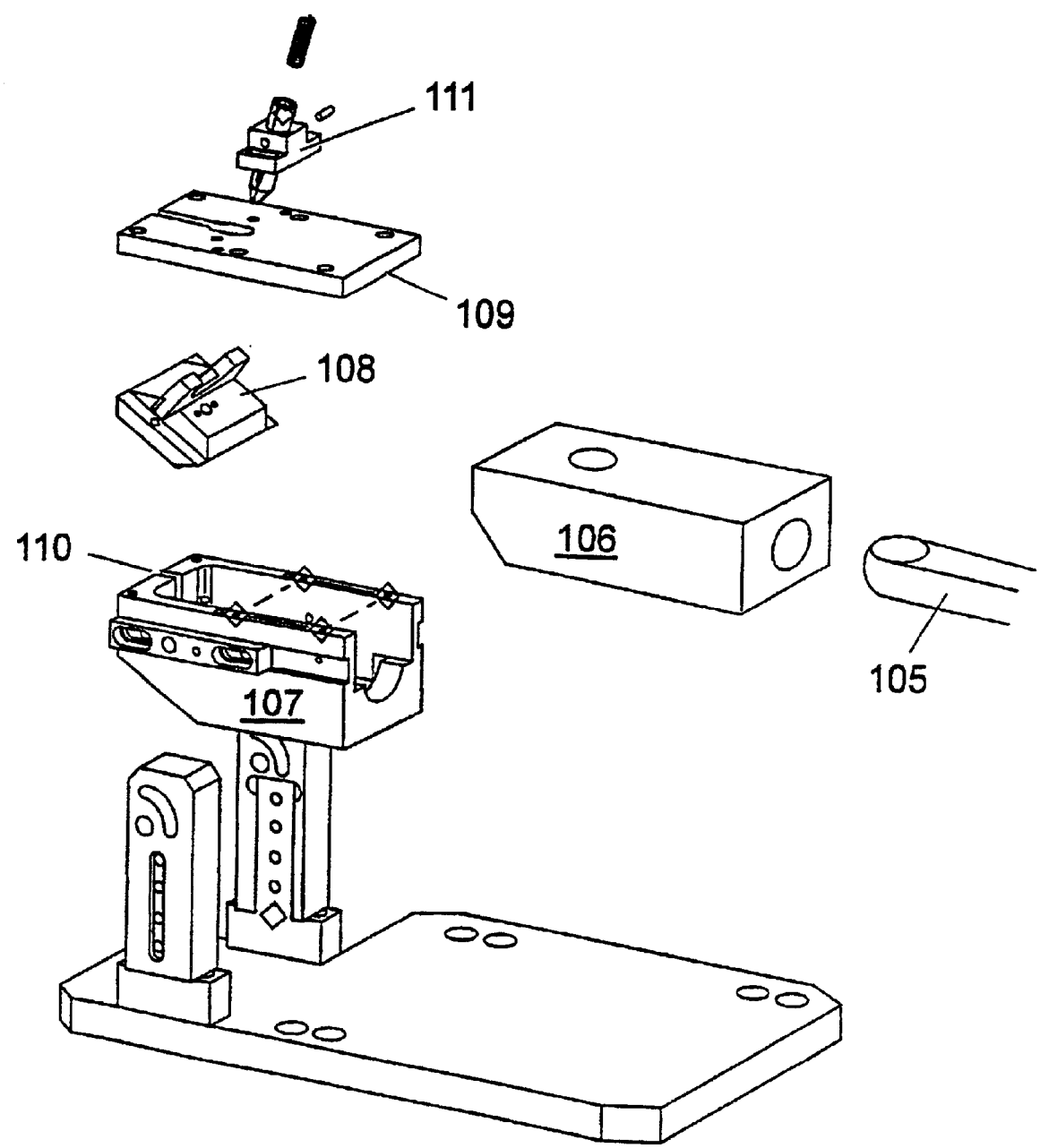
FIG. 13 is a perspective view of a finger interface apparatus with removable inserts that are moulded to fit one individual.
Figure 13A:
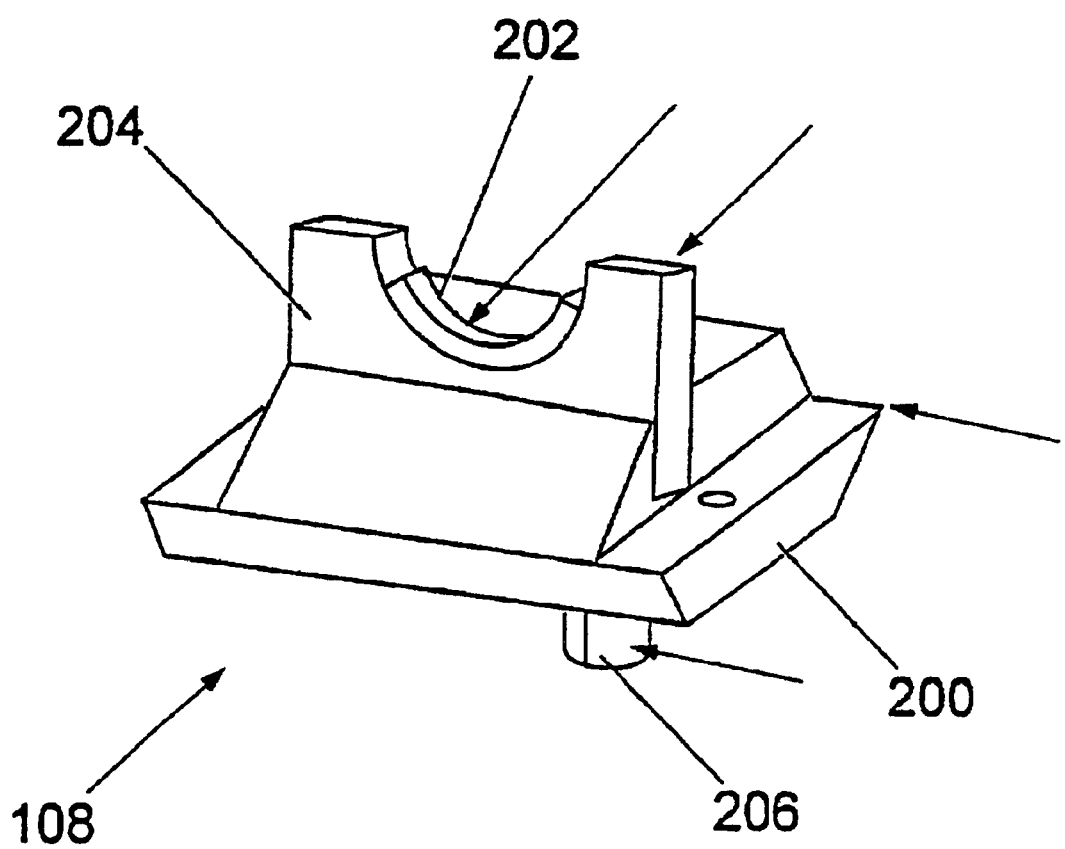
FIG. 13A shows part of the apparatus of FIG. 13 in greater detail.

Referring to FIG. 13, another method of using a finger as the body part and including removable inserts is shown. A finger 105 is inserted into an insert 106 that is used to customize the finger holder to a particular finger. The moulded insert 106 is placed into a housing 107. The finger 105 is placed against a semi-cylindrical acoustic detector in a module 108 which is also attached to the housing 107. A cover 109 for the housing 107 contains a mechanism 111 to apply constant force to the finger 105. The light beam 110 is introduced into the finger 105 using a suitable optical distribution system (not shown). FIG. 13A shows the module 108 in greater detail. A base 200 carries a part-cylindrical piezo transducer 202 on a support 204. 206 indicates a coaxial connector to communicate the transducer signal.

Figure 14:
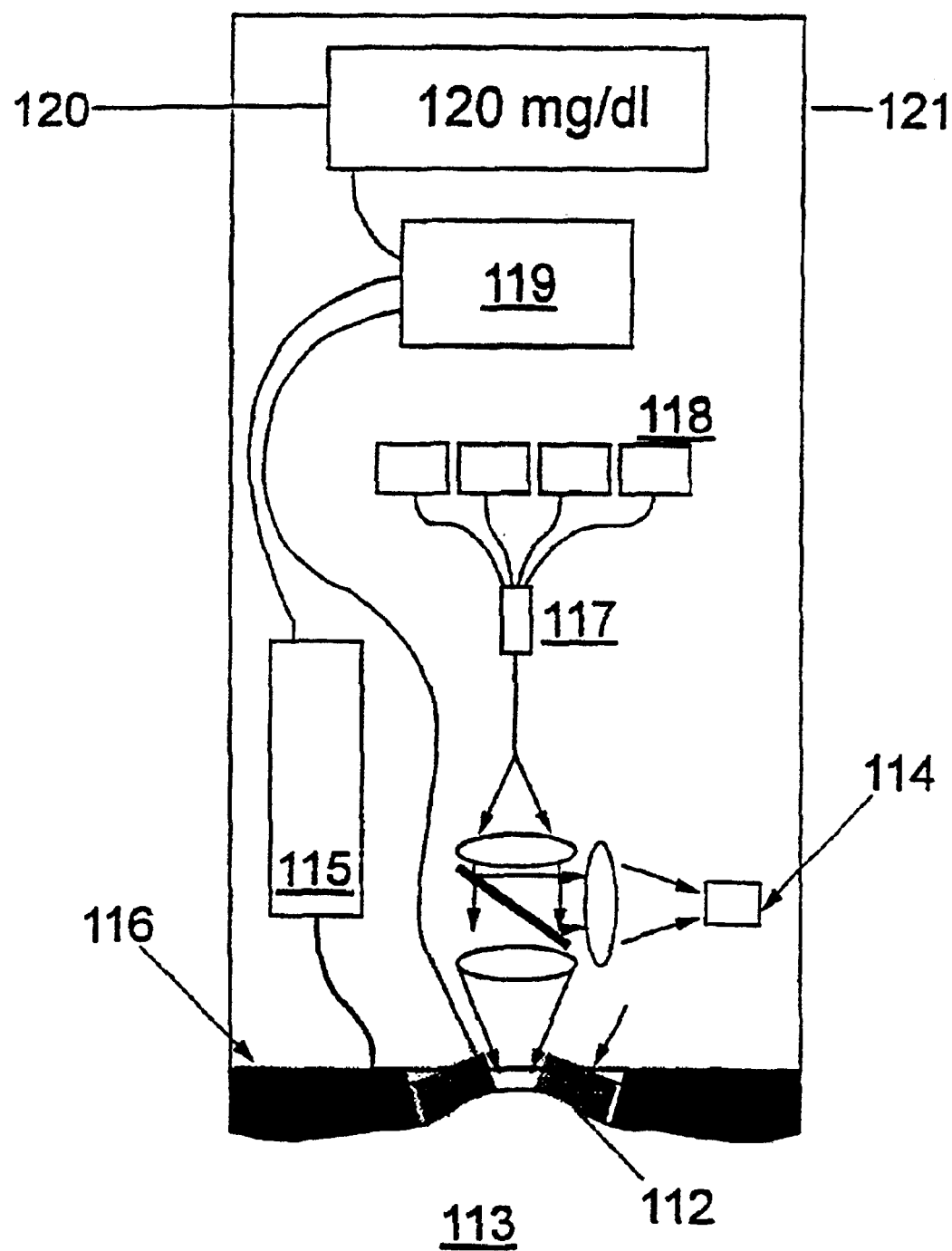
FIG. 14 is a schematic of a semi-spherical detector that contains a hole for the light beam, with a vacuum system and a fiber distribution system.

FIG. 14 shows a schematic of an alternative to the vacuum arrangement shown in FIGS. 8 and 9. In this system a photoacoustic reader 121 is placed against the skin 113 with a semi-spherical detector 112 in contact with the skin 113. A vacuum pump 115 and vacuum seal 116 create a negative pressure and pull the skin 113 against the detector 112. Processing electronics 119 energizes light sources 118 and an optical distribution system 117 routes the light to the body part through a hole in the top of the semi-spherical detector 112. The optical distribution system 117 directs a small portion of the light to a reference detector 114. The processing electronics 119 measures the signal from the acoustic detector 112 and the reference detector 114 for each optical source 119 and calculates the glucose value. The value is displayed on a display 120.

Figure 15:
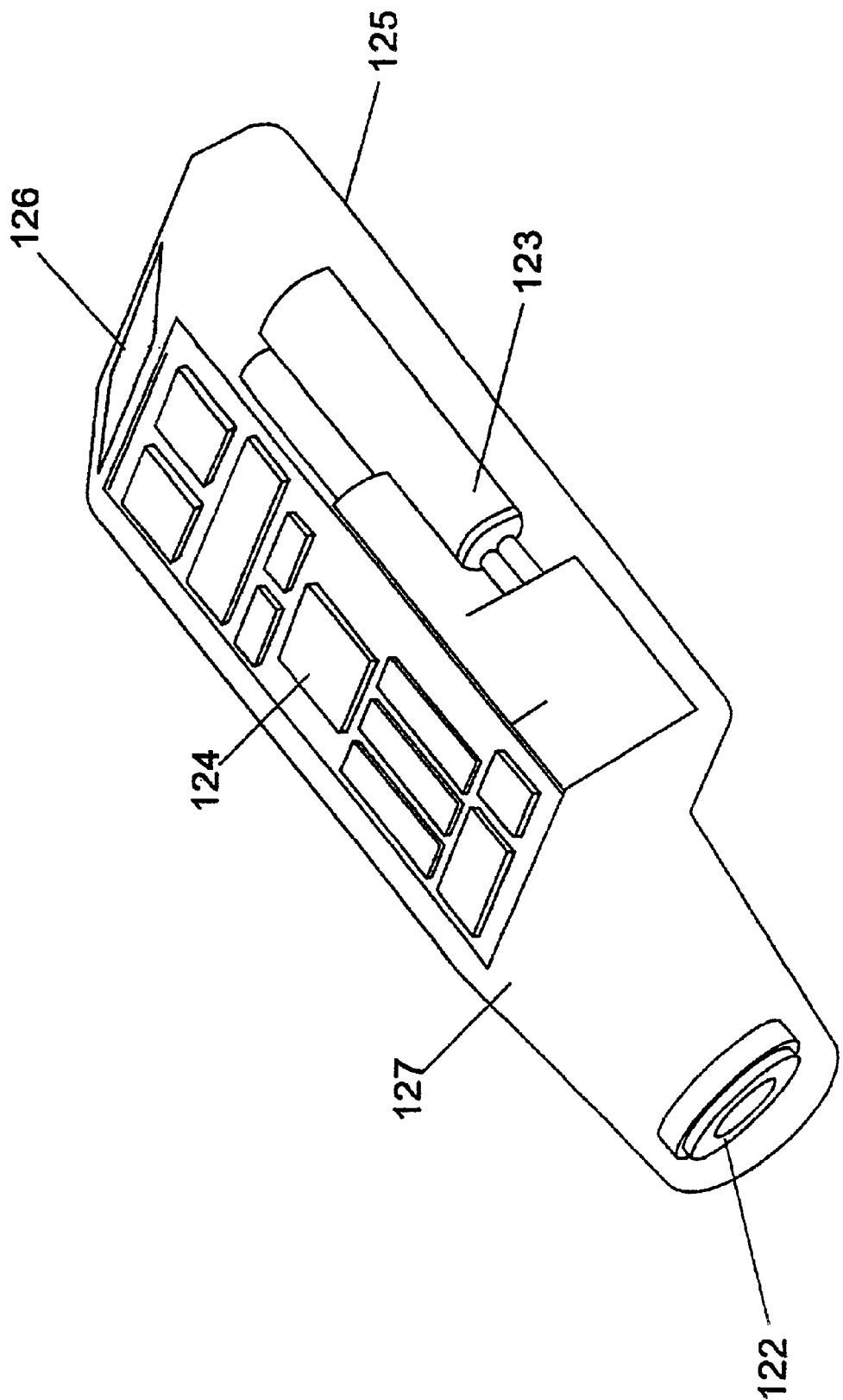
FIG. 15 is a perspective view showing one form of the instrument utilizing the vacuum body interface, a semi-spherical detector and the multiple laser source with lenses and mechanical housing.

FIG. 15 shows a similar system 125, only using another type of optical distribution system 127. Again a vacuum pump 123 creates a negative pressure which draws the skin up to an acoustic detector 122. Processing electronics 124 signals light sources in optical distribution system 127 to illuminate and a signal is generated at acoustic detector 122. The processing electronics 124 calculates the proper value and displays it on a display 126.

Figure 16:
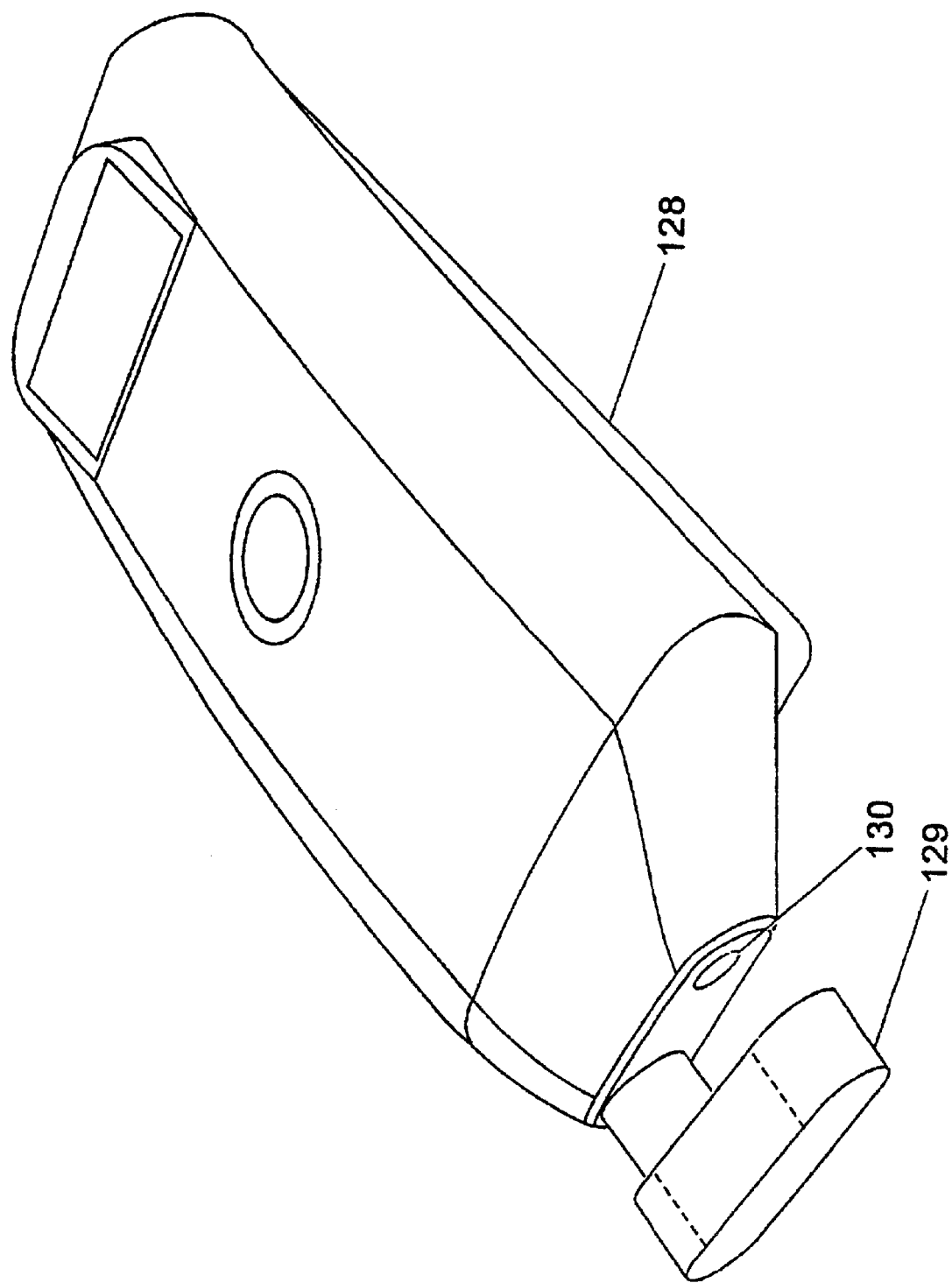
FIG. 16 is a perspective view showing one form of the instrument using an ear lobe body interface, with the added feature of being able to manipulate the pressure on the ear lobe.

FIG. 16 shows an alternative arrangement of a photoacoustic reader. In this system 128, the vacuum system is replaced with an ear squeeze mechanism 129 which applies pressure to the ear. An acoustic detector 130 detects the signals from the ear lobe.

In the most straightforward forms of the invention, a single analyte such as glucose in blood can be measured by using light of selected wavelengths and by measuring the area or the amplitude of the received acoustic pulse. It is preferable to make each measurement by using a train of pulses, for example about 100 pulses, and averaging the results in order to minimise the effects of noise and pulse effects in the blood flow.

The accuracy of the detection system is governed, in part, by the Signal to Noise Ratio (SNR) of the system. Variations in the intensity and duration of the light source can cause the acoustic signal to contain variations. A normalization technique such as taking the ratio of the acoustic signal to the optical signal, can significantly reduce the effect of the source variations, thereby improving the signal to noise ratio of the system. The optical signal can be measured with a reference detector, or several reference detectors, one for each source or one for a wavelength range. An equation describing this type of normalization follows:

$$\text{Normalized Signal} = \frac{\text{Acoustic Signal}}{\text{Optical Signal}}$$

In some cases the relationship between the optical signal land the acoustic signal changes with wavelength and light intensity. When this is the case the accuracy of the measurement can be further enhanced by determining the energy dependence of the photoacoustic signal. This may be determined by establishing the specific relationship between the photoacoustic signal land the incident energy from a set of measurements and using this relationship to compensate for the non linear response. An equation describing this type of normalization is as follows:

$$\text{Normalized Signal} = \frac{\text{Acoustic Signal}}{\text{Scaling Factor} * \text{Optical Signal} + \text{Offset}}$$

Other normalization methods can also apply. The time interval between the optical pulse and the detection of the acoustic signal may be used to characterise physical properties such as the velocity of sound in the tissue. In addition, in another embodiment of the device the damping of the acoustic oscillations may be used to monitor the elastic properties of the tissue and, in particular, the compressibility. Both of these aspects may be used in the person to person calibration of the photoacoustic response.

More complex analysis of the received acoustic energy is possible. For example, a time-gating technique may be used to derive measurement at varying depths within the tissue being examined. Alternatively, an array of detectors can be employed to determine the profile of the absorption of the acoustic signal at different depths and locations. This depth profile will change with the absorption coefficient and could be used as additional information to determine the analyte concentration. It is also possible to derive information relating to a number of analytes of interest by more sophisticated analysis of the received acoustic energy wave forms, for example by analysis of the frequency spectrum by Fourier transform or wavelet analysis techniques.

Alternatively, or in combination with the frequency techniques and multiple detectors, multiple light sources can aid in the determination of the concentration of a number of analytes.

There are a number of tissue features which may vary from person to person or with in the same person over time which impact the photoacoustic signal observed. To obtain an accurate measurement of a given analyte, such as glucose, it may be helpful to also determine the concentration of other analytes such as haemoglobin which may act as interferants. One approach is to generate several distinct photoacoustic signals using excitation light of several different wavelengths. For example, excitation light of a wavelength of which haemoglobin absorbs strongly but glucose has little if any absorption could be sued to obtain a measure of the haemoglobin concentration with which to normalize the effect of haemoglobin on measurements made on different persons or on the same person at different times. These measurements which are to be normalized might be based on the photoacoustic signal generated by light of a wavelength at which glucose absorbs.

It is also possible to measure the concentration of such interferants by other means, such as infrared light absorption, and thus normalize or correct the photoacoustic signal representative of the desired analyte for variations in these interferants. Thus, for example, the photoacoustic signal representative of glucose could be corrected for variations in haemoglobin concentration determined by optical absorption techniques such as those taught in U.S. Pat. No. 5,702,284.

For the reliable and reproducible determination of glucose a signal to noise ratio of at least 10,000 is recommended. In this regard water is typically present in human tissue of a concentration of about 50 molar while glucose is present at a concentration of about 5 millimolar in a normal individual.

Apparatus and method embodying the present invention have been found to yield accurate and repeatable results. In the case of blood glucose measurement, the clinical range of glucose concentration is approximately 5–10 m mol/l in healthy subjects, and up to 40 m mol/l in diabetics. An analysis based on simple absorption models suggests that the change in photoacoustic signal over this range might be as little as 0.2%. The present invention has been found to provide a change in photoacoustic signal of up to 140% for a change in glucose concentration of 15 m mol/l.

The precise mechanisms involved are not at present fully understood. It is believed, however, that absorption occurs primarily in body plasma and is modified by the presence of glucose, and that this affects beam geometry.

EXAMPLE

Figure 17:
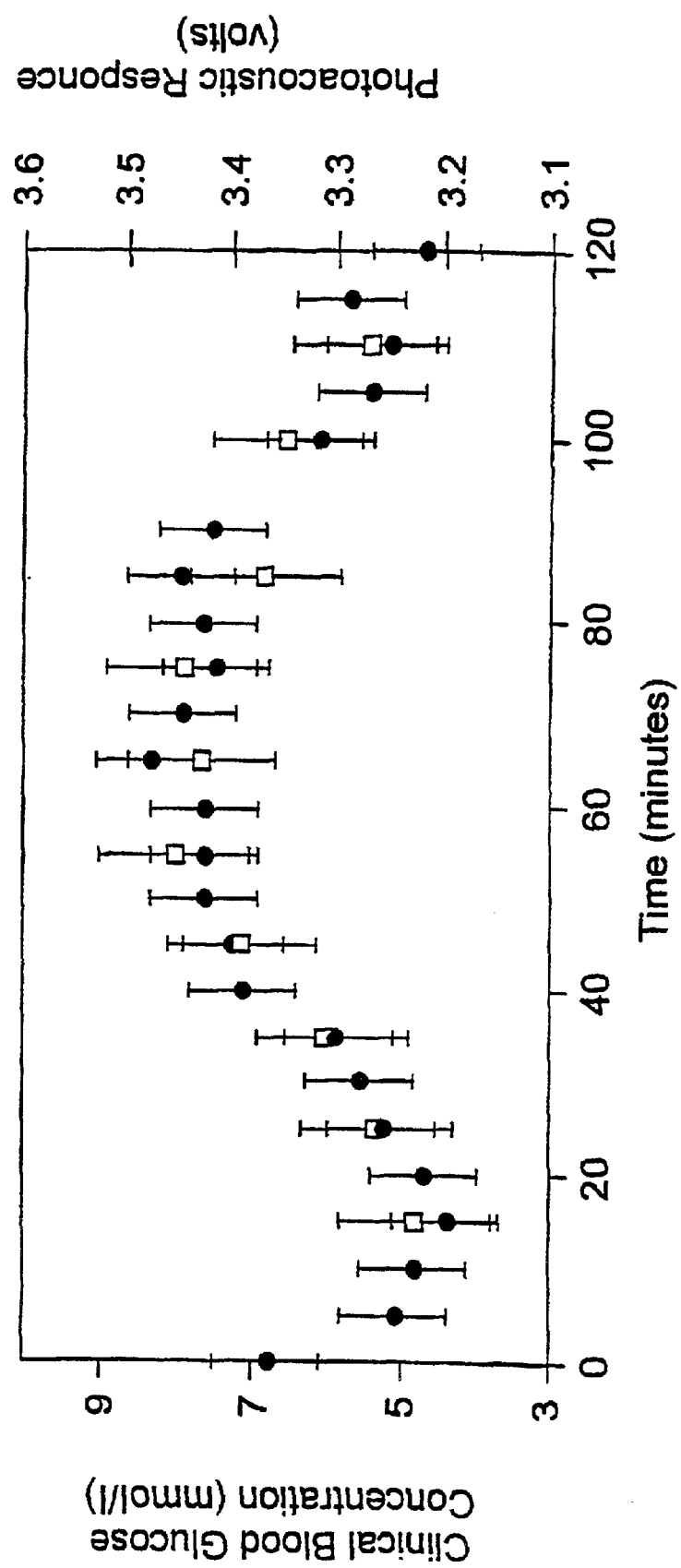
FIGS. 17, 18 and 19 are graphs illustrating an example.
Figure 18:
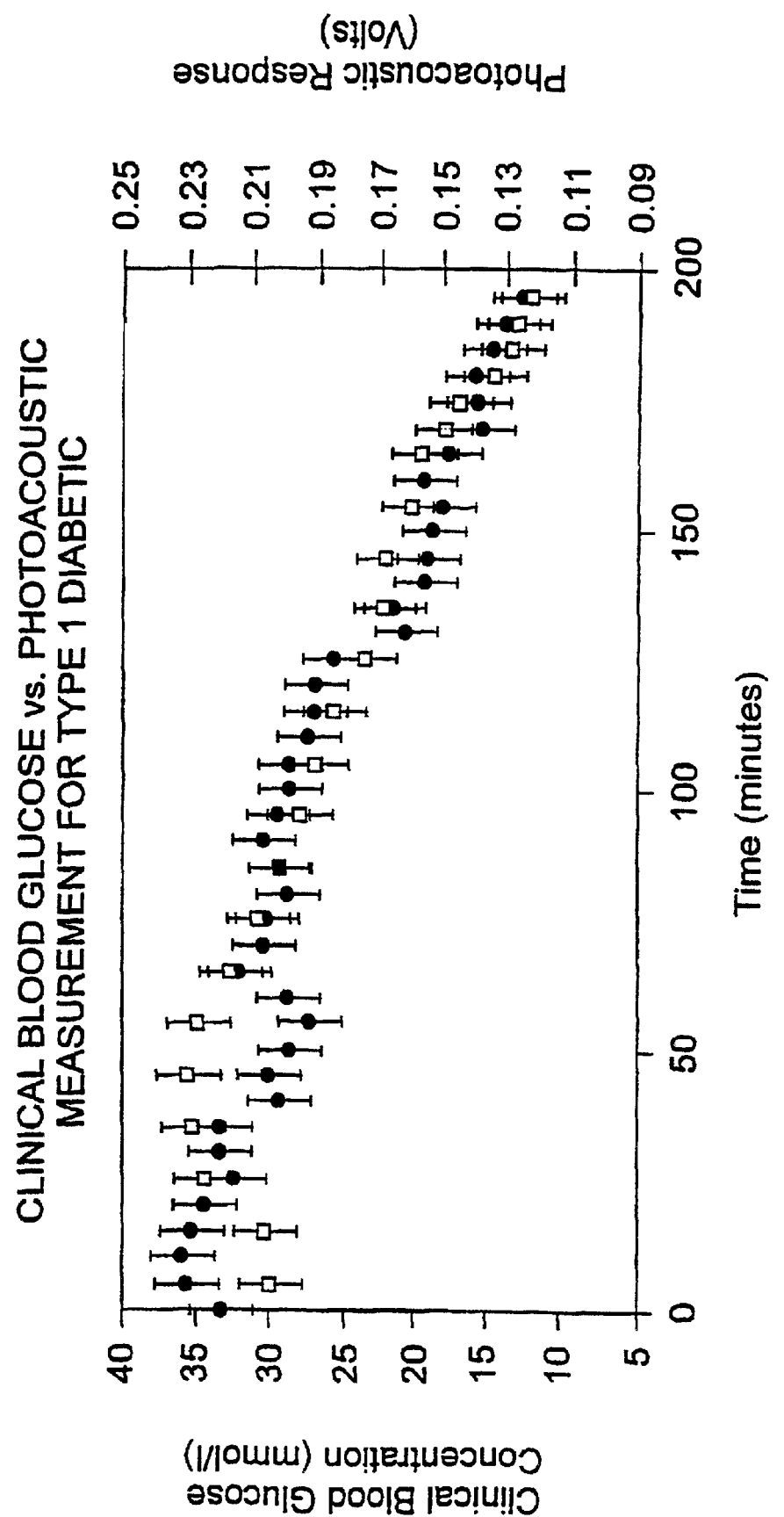
Figure 19:
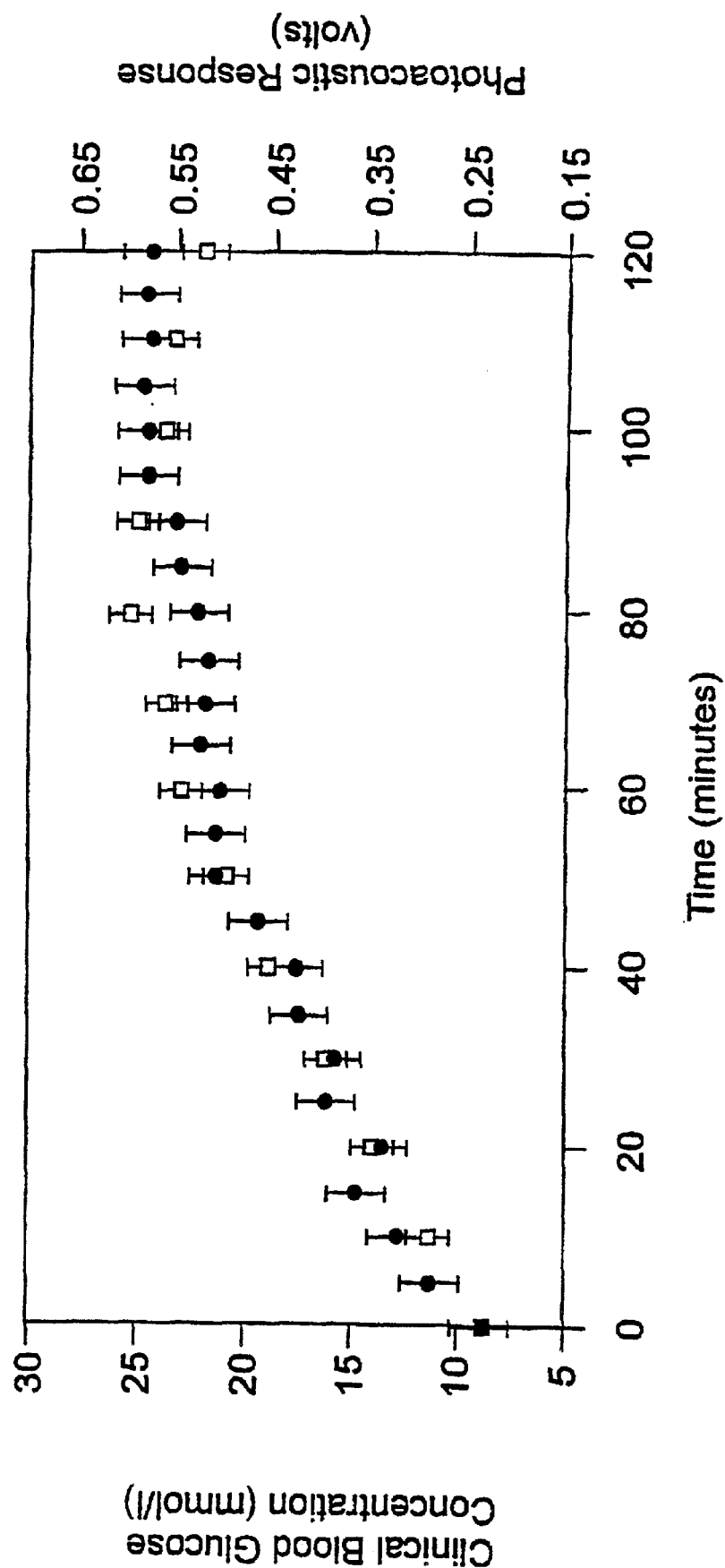

The blood glucose levels of three individuals, one normal individual, one type 1 diabetic and one type 2 diabetic, were followed over a two hour period following each individual taking about 75 grams of glucose orally in an aqueous solution by both photoacoustics and direct blood measurement. The results are reported in FIGS. 17, 18 and 19. Photoacoustic measurements were made every five minutes and blood measurements were made very ten minutes. The blood samples were venous blood samples analysed by the standard glucose oxidase method using a Yellow Springs instrument. The error bands for the blood measurements were derived from the literature accompanying the testing instrument while those for the photoacoustic results were based on the averages taken over 1000 pulses. The results were obtained from a configuration similar to that illustrated in FIG. 1 in which 10 was an end of a 1 km multimode fibre Optic cable which was placed against the finger 12. The other end received 600 nanosecond pulses of 1040 nanometer light from a Q switched Nd:YAG laser delivering 2.7 micro joules per pulse for each measurement. Raman interactions in the fibre caused the production of light an additional wavelengths as set forth in the following table:

| Wavelength in nm | Average pulse energy in microJoules | Pulse width in ns | Approximate bandwidth in nm |
|---|---|---|---|
| 1064 | 2.7 | 600 | 4 |
| 1120 | 2.25 | 500 | 6 |
| 1176 | 2.0 | 450 | 8 |
| 1240 | 1.5 | 425 | 12 |
| 1308 | 0.85 | 400 | 15 |
| 1390 | 0.3 | 350 | 20 |
| 1450 | 0.1 | 350 | 20 |
| 1500 | 0.2 | 350 | 20 |
| 1550 | 0.18 | 360 | 20 |

The resulting photoacoustic signal was detected by a 5 mm disc transducer with a lead backing and fed to an amplifier and an oscilloscope. The transducer was generally placed as 16 in FIG. 1 but was not precisely parallel to the beam axis; its detection plane was at an angle of about 20 degrees to the beam axis. The photoacoustic signal was evaluated in terms of the difference in voltage signal from the positive peak of the compression to the negative peak of the relaxation of the acoustic pulse.

The change in photoacoustic response correlated well with the change in blood glucose concentration over the two hour measurement period. A correlation of 0.89 was achieved on samples ranging from 4 to 35 m mol/l.

Other modifications and improvements may be made to the foregoing embodiments within the scope of the present invention as defined in the claims.

What is claimed is:

1. A sensor head for use in photoacoustic in vivo measurement, comprising a housing shaped to engage a selected body part, light transmission means terminating in said housing so as to transmit light energy from a light source to enter the body part along a beam axis, and acoustic transducer means mounted in the housing to receive acoustic waves generated by photoacoustic interaction within the body part, the acoustic transducer means being disposed in the housing to receive said acoustic wave in a direction of high acoustic energy, wherein said direction of high acoustic energy is a direction other than the forward direction of said beam axis.

2. A sensor head according to claim 1, in which the acoustic transducer means is arranged at least partially perpendicular to the optical beam axis.

3. A sensor head according to claim 2, for use where the selected body part is the distal portion of a finger, in which the housing includes a generally half-cylindrical depression in which the finger may be placed with the light transmission means aimed at the end of the finger.

4. A sensor head according to claim 1, in which the acoustic transducer means comprises a piezoelectric transducer which is of a semi-cylindrical shape.

5. A sensor head according to claim 1, in which the acoustic transducer means comprises a piezoelectric transducer which is provided with a backing of lead or other dense material.

6. A sensor head according to claim 5, in which said backing has a rear surface shaped to minimize internal acoustic reflection.

7. A sensor head according to claim 1, in which the acoustic transducer means comprises a capacitor-type detector.

8. A sensor head according to claim 1, in which the acoustic transducer means comprises a piezoelectric transducer arranged generally perpendicular to the optical axis to detect the acoustic wave which is propagating in a direction opposite to the direction of propagation of the light beam.

9. A sensor head according to claim 8, in which the acoustic transducer means is part-spherical with an aperture to allow access for the light beam.

10. A sensor head according to claim 1, including a surface wave detector for characterizing tissue properties.

11. A sensor head according to claim 1, including means for ensuring a consistent contact pressure between a selected body part and the acoustic transducer means.

12. A sensor head according to claim 11, for use where the selected part is the distal portion of a finger, said means being provided by mounting a portion of the housing engaged by the finger in a resiliently biased fashion against the remainder of the housing, and providing means to ensure that measurement is effected when a predetermined force or pressure is applied by the subject against the resilient bias.

13. A sensor head according to claim 11, for use where the selected part is the earlobe, said means being provided by two plates, between which the earlobe may be placed, and means for pressing the plates together to apply pressure to the ear.

14. A sensor, head for use in photoacoustic in-vivo measurements, comprising a housing shaped to receive a removable insert; a removable insert that engages a selected body part, the insert being fitted to an individual, allowing for a range of sizes of body parts to be used; light transmission means terminating in or near said removable insert so as to transmit light energy from a light source to enter the body part along a beam axis; and an acoustic transducer means mounted in the housing or in the removable insert to receive acoustic waves generated by photoacoustic interaction within the body part, the acoustic transducer means being disposed in the housing or insert to receive said acoustic waves in a direction of high acoustic energy, wherein said direction of high acoustic energy is a direction other than the forward direction of said beam axis.

15. A method of measuring a biological parameter in a subject, the method comprising the steps of:

directing one or more pulses of optical energy from the exterior into the tissue of a subject along a beam axis, the optical energy having a wavelength selected to be absorbed by tissue components of interest, thereby to produce a photoacoustic interaction;

detecting acoustic energy resulting from said photoacoustic reaction by means of a transducer positioned to intercept acoustic energy propagating in a direction other than the forward direction of said beam axis; and deriving from said detected acoustic energy a measure of the parameter of interest, wherein said method further comprises the steps of correcting measurement of an analyte based on a photoacoustic signal obtained from a living being comprising determining the concentration of other constituents in the living being which have a significant effect on the photoacoustic signal and tend to vary from individual to individual or over time, and adjusting the measurement to remove the effect of variations in the concentrations of said other constituents.

16. The method of claim 15, in which the parameter of interest is blood glucose, and the optical energy has a wavelength in the range of approximately 600 nm to 10,000 nm and a pulse duration of the order of 5 to 500 ns.

17. The method of claim 15, in which a train of pulses is applied and the detected signals are averaged to derive said measure.

18. The method of claim 15, in which said measure is derived from the energy of the detected signal.

19. The method of claim 15, in which the optical energy is directed into a body part which is substantially composed of soft tissue and free of bone.

20. Apparatus for measuring a biological parameter in a subject, the apparatus comprising:

means for directing one or more pulses of optical energy from the exterior into the tissue of a subject along a beam axis, the optical energy having a wavelength selected to be absorbed by tissue components of interest, thereby to produce a photoacoustic interaction;

transducer means arranged to detect acoustic energy resulting from said photoacoustic reaction by intercepting acoustic energy propagating in a direction other than the forward direction of said beam axis; and means for deriving from said detected acoustic energy a measure of the parameter of interest.

21. Apparatus according to claim 20, in which said directing means includes means for receiving a selected body part such that the optical energy is directed into a portion of the subject's body which is substantially free of bone.

* * * * *